(12) United States Patent
Groneberg-Nienstedt et al.

(10) Patent No.: US 8,916,222 B2
(45) Date of Patent: *Dec. 23, 2014

(54) METHOD AND DEVICE FOR PRODUCING SHAPED MEAT PORTIONS FROM WHOLE NATURAL MEAT PIECES

(75) Inventors: Petra Groneberg-Nienstedt, Haltern am See (DE); Michael Gutmann, Haltern am See (DE)

(73) Assignee: Nienstedt GmbH, Haltern am See (DE)

( * ) Notice: Subject to any disclaimer, the term of this patent is extended or adjusted under 35 U.S.C. 154(b) by 1097 days.

This patent is subject to a terminal disclaimer.

(21) Appl. No.: 12/280,064

(22) PCT Filed: Feb. 20, 2007

(86) PCT No.: PCT/EP2007/051627
§ 371 (c)(1),
(2), (4) Date: May 13, 2009

(87) PCT Pub. No.: WO2007/096363
PCT Pub. Date: Aug. 30, 2007

(65) Prior Publication Data
US 2009/0246333 A1     Oct. 1, 2009

(30) Foreign Application Priority Data

Feb. 20, 2006 (DE) .......................... 10 2006 008 132
Mar. 4, 2006 (DE) .......................... 10 2006 021 139

(51) Int. Cl.
*A23P 1/10* (2006.01)

(52) U.S. Cl.
USPC ............................. 426/512; 426/513; 426/518

(58) Field of Classification Search
USPC ......... 426/512–513, 515, 524, 231, 389, 281, 426/518; 425/256, 395, 397
See application file for complete search history.

(56) References Cited

U.S. PATENT DOCUMENTS

| | | | |
|---|---|---|---|
| 2,521,995 | A | 9/1950 | Priddy |
| 2,798,814 | A | 7/1957 | Rivoche |

(Continued)

FOREIGN PATENT DOCUMENTS

| | | |
|---|---|---|
| DE | 22 35 517 A1 | 1/1973 |
| DE | 198 06 391 A1 | 8/1999 |

(Continued)

OTHER PUBLICATIONS

U.S. Appl. No. 12/280,056, filed May 26, 2009, Groneberg-Nienstedt et al.

(Continued)

*Primary Examiner* — Steven Leff
(74) *Attorney, Agent, or Firm* — Panitch Schwarze Belisario & Nadel LLP

(57) ABSTRACT

A device for producing shaped meat portions, the device including a sorting device for sorting meat into a first set of pieces having a weight which is below a desired weight, a second set of pieces having a weight which corresponds to a desired weight, and a third set of pieces having a weight which is above a desired weight. The device further includes a cutting device which cuts each of the third set of pieces to a desired weight so that the cut pieces having a desired weight define a set of selected meat pieces. A transport device transports the set of selected meat pieces and a freezing facility through which the transport device conveys the set of selected meat pieces and which freezes the set of selected meat pieces. The device further including a shaping device which presses or presses and punches the frozen set of selected meat pieces in a mold and thus transforms the frozen set of selected meat pieces into a final shape or a plurality of final shapes, wherein the shaping device produces in a controlled manner meat portions having a predefined weight and a predefined three-dimensional shape.

11 Claims, 1 Drawing Sheet

(56) References Cited

U.S. PATENT DOCUMENTS

| | | | |
|---|---|---|---|
| 3,728,136 A * | 4/1973 | Langlands | 426/513 |
| 3,892,988 A | 7/1975 | Gran | |
| 4,036,997 A | 7/1977 | VerBurg | |
| 4,276,314 A | 6/1981 | Anderson | |
| 4,626,436 A | 12/1986 | Bradley et al. | |
| 4,868,951 A | 9/1989 | Akesson et al. | |
| 4,973,492 A | 11/1990 | Gibson | |
| 5,223,297 A | 6/1993 | Theys et al. | |
| 5,518,746 A | 5/1996 | Diaz | |
| 5,690,989 A * | 11/1997 | Clarke et al. | 426/641 |
| 6,826,989 B1 | 12/2004 | Wattles et al. | |
| 2003/0044501 A1 * | 3/2003 | Groneberg-Nienstedt | 426/513 |
| 2003/0113422 A1 | 6/2003 | Groneberg-Nienstedt et al. | |
| 2004/0231480 A1 | 11/2004 | Wattles et al. | |
| 2005/0181099 A1 | 8/2005 | Tazuke et al. | |
| 2005/0282482 A1 | 12/2005 | Groneberg-Nienstedt | |
| 2008/0038426 A1 | 2/2008 | Groneberg-Nienstedt et al. | |
| 2009/0029027 A1 | 1/2009 | Groneberg-Nienstedt et al. | |
| 2009/0220660 A1 | 9/2009 | Meunier | |
| 2009/0246333 A1 | 10/2009 | Groneberg-Nienstedt et al. | |

FOREIGN PATENT DOCUMENTS

| | | |
|---|---|---|
| DE | 101 41 989 A1 | 4/2003 |
| DE | 101 64 637 A1 | 6/2003 |
| DE | 102 20 006 A1 | 11/2003 |
| DE | 10 2005 016 159 A1 | 10/2006 |
| EP | 0 168 909 A2 | 1/1986 |
| EP | 0 288 592 A1 | 11/1988 |
| EP | 1 470 754 A1 | 10/2004 |
| EP | 1 156 720 B1 | 2/2005 |
| EP | 1 595 456 A1 | 11/2005 |
| FR | 2 847 427 A1 | 5/2004 |
| GB | 2 280 869 A | 2/1995 |
| WO | WO 97/10717 A1 | 3/1997 |
| WO | WO 03077662 A1 * | 9/2003 |
| WO | WO 2006/053601 A1 | 5/2006 |
| WO | WO 2006/105821 A1 | 10/2006 |
| WO | WO 2007/085773 A1 | 8/2007 |

OTHER PUBLICATIONS

U.S. Appl. No. 12/739,626, filed Apr. 23, 2010, Groneberg-Nienstedt.

Author anonymous, Abstract of "Finger foods—new process offers exciting possibilities," FTSA database-Database Accession No. 86-3-10-g0028 regarding Food Review, vol. 13, No. 1, 1986, p. 19, one page.

Office Action mailed on Jan. 30, 2012 regarding U.S. Appl. No. 12/280,056.

Office Action mailed on Nov. 21, 2012 regarding U.S. Appl. No. 12/739,626.

Office Action mailed on Apr. 23, 2013 regarding U.S. Appl. No. 12/280,056.

* cited by examiner

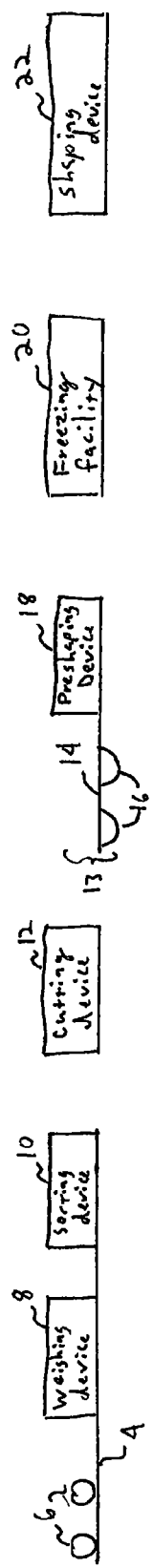

METHOD AND DEVICE FOR PRODUCING SHAPED MEAT PORTIONS FROM WHOLE NATURAL MEAT PIECES

Applicants claim, under 35 U.S.C. §119, the benefit of priority of 1) the filing date of Feb. 20, 2006 of a German patent application, copy attached, Serial Number 10 2006 008 132.3, filed on the aforementioned date, and 2) the filing date of May 4, 2006 of a German patent application, copy attached, Serial Number 10 2006 021 139.1, filed on the aforementioned date, the entire contents of each of which are incorporated herein by reference.

BACKGROUND OF THE INVENTION

1. Field of the Invention

The present invention relates to a device and a method for producing shaped meat portions from whole natural meat pieces, which includes two separate sub-processes carried out one after the other: On the one hand meat pieces are checked and are brought to a target weight without any shaping cutting being required, and on the other hand meat pieces are checked and are transformed into a predefined, three-dimensional product.

This method includes the following method steps:
introducing pieces of whole natural meat into a processing line,
rejecting those meat pieces which do not reach a desired weight of the meat portions, or combining clusters of meat pieces from individual meat pieces having a fraction of the desired weight,
cutting those meat pieces having a weight which exceeds a desired weight of the meat portions,
selecting those meat pieces or clusters of smaller meat pieces having a weight which corresponds to a desired weight,
freezing the selected meat pieces to form frozen meat portions, and
shaping the frozen meat portions by placing them in a shaping cavity and pressing them or pressing and punching them to form the shaped meat portions.

This method is intended to encompass the processing of all types of natural meat, in particular beef, pork, mutton, lamb, game, poultry or fish, including the respective offal.

2. Description of the Related Art

In the food industry, it is known to cut natural meat pieces to the correct weight and shape in one single step. This is carried out for example by cutting by a water jet or conventionally using knives. One disadvantage here is that a large quantity of off-cuts or undesired products are obtained which cannot be used in the rest of the process. Furthermore, the height profile of the product can be controlled only to a limited extent.

A method of this type is known from DE 101 64 637 A1. In this method, whole natural meat pieces are sorted and cut to size where necessary so that the required portions can be produced. If the minimum weight is not reached, a number of smaller meat pieces are processed together.

However, this known method has the disadvantage that the customer often asks for a piece of meat which includes not several parts but rather one single piece of natural meat. The reason for this may lie on the one hand in the notion expressed by the subsequent end customer that the meat should be in one piece "like an wiener schnitzel", and on the other hand in the risk that the individual parts will fall apart again during the subsequent cooking process.

A disadvantage of the known methods is that too many off-cuts are obtained which cannot be used in the process if the portion or portions are to be made from just one single piece. The present invention overcomes this disadvantage in that the weight control and shape control are carried out in separate sub-processes. This results in much lower restrictions with regard to the shape of the meat portions during weight control and/or a much higher flexibility when designing the three-dimensional final shape than in the known methods.

However, if the part that is too small cannot be made up to the desired weight by adding another part, then it is only possible to use those parts which right from the start either already have precisely the required size or which exceed the desired weight, so that the desired weight can be achieved by cutting off part of the natural meat.

Another disadvantage of this method is that the natural meat pieces are cut to the correct weight, with the size of the piece initially playing only a subordinate role. A very thin piece could thus pass the weight check and would then be deep-frozen, even though this piece would not really be suitable for the shaping process in the shaping machine since, due to the fact that its width is much too large, it cannot be pressed into the shaping cavity without part of the product shearing off and thus no longer being further processed. This would mean that the required quantity of meat would no longer be contained in the end product, thereby giving rise to a quality problem.

DE 101 41 989 A1 discloses a method for punching a meat portion having a defined size out of a mass preshaped into a slab. In this method, the desired pieces are punched out of the slab-shaped material already in the subsequently desired shape, for instance a round disc for a special hamburger.

The disadvantage of this method is that, particularly in the case of smaller pieces, the slab of material is naturally very small so that usually only one piece can be punched out of the raw material, while the remainder which cannot be used has to be supplied to another method, even though the total quantity of the processed piece would have provided sufficient volume for a second piece.

A similar method is also known from DE 10 2005 016 159 A1, in which again a number of sub-pieces are combined to form a common part, from which the individual shaped bodies can then be punched out.

Also generally known is a method in which the natural meat piece is rolled in a first step to form a flat shaped piece, and the desired shape is cut out in a second step. The disadvantages of this method are the poor control of the shape of the end product, the reduced possibility of obtaining a genuine three-dimensional product, and the fact that there is still a large quantity of off-cuts which cannot be used in the further process.

SUMMARY AND OBJECTS OF THE INVENTION

An object of the present invention is therefore to provide a method for producing shaped meat portions from whole natural meat pieces, in which the shaped meat portion is produced in two steps so that it is given a predefined weight and a predefined shape without creating unnecessary off-cuts. Another object of the present invention is also to achieve the predefined weight in such a way that there are minimal restrictions with regard to the desired meat portions and such as to obtain the greatest possible flexibility in terms of the design of the predefined three-dimensional shape of the meat portion.

According to the present invention, these objects are achieved in that the selected meat pieces or clusters of meat pieces are placed in a mould prior to freezing, the base surface area of which mould corresponds to the base surface area of the shaping cavity or is smaller than the base surface area of the shaping cavity, and in a controlled manner and under the action of pressure the resulting shaped meat pieces or clusters of meat pieces in the frozen state are made into meat portions having a predefined weight and a predefined three-dimensional shape. These weight-controlled and shape-controlled meat pieces can then be supplied to further processes such as e.g. cooking, coating with breadcrumbs, garnishing, deep frying, freezing, cooling.

Further details and advantages of the present invention will become apparent in the course of the following description of exemplary embodiments by the drawing figure.

BRIEF DESCRIPTION OF THE DRAWING

FIG. 1 schematically shows an embodiment of a device for producing shaped meat portions in accordance with the present invention.

DESCRIPTION OF THE PREFERRED EMBODIMENT(S) OF THE INVENTION

FIG. 1 schematically shows an embodiment of a device 2 for producing shaped meat portions. In particular, the device includes a conveyor belt 4 that directs meat pieces 6 to a weighing device 8 from which a sorting device 10 processes the meat pieces depending on their weight determined by the weighing device 8. For those meat pieces having a weight that exceeds a desired weight, they are cut to obtain the desired weight by cutting device 12. After the cutting has been performed, those meat pieces that have the desired weight as determined by the sorting device 10 or as a result of the cutting performed at cutting device 12, the meat pieces are preshaped by preshaping device 18 by placing or pressing the meat pieces into freezing cavities, such as shaping nests 16 of the transport belt 14 of transport device 13. The preshaped meat pieces are frozen via freezing facility 20 and then shaped via shaping device 22. More details of the device 2 and its operation are given below.

According to the present invention, after having been brought to a predefined weight, the meat pieces are frozen and then reshaped. Firstly, the meat pieces 6 are weighed and sorted via the weighing device 8 and sorting device 10, respectively. This may take place manually or by a machine, wherein in the case of manual weighing it is then possible for the cutting process to take place at the same time. In the automatic method, the meat pieces are supplied for example via a conveyor belt 4 which has an integrated weighing device 8. The integrated weighing device determines the weight of the meat pieces based on a predefined density value and detected volumes of the meat pieces. Via pivoting arms of the sorting device 10 known from logistics, the piece in question is conveyed away by the conveyor belt 4 or allowed to pass in a controlled manner, depending on the result of the weighing. Meat pieces having a weight that is too low are then rejected and supplied to another processing method or combined to form clusters which can in turn be supplied as a meat piece to the method described here.

The pieces which exceed the desired weight are cut to this desired weight in order to process the required mass of meat for all the processed pieces. This step is referred to as portion control, and therefore the meat pieces are processed in the correct portion size with the weight being the decisive criterion for allowing the piece to enter the processing method. However, no cutting-to-shape is carried out here, so that off-cuts resulting from the required shaping can be avoided or minimised.

The cutting may take place manually by knives or automatically via the cutting device 12, in the latter case in a conventional manner or via ultrasound, by means of a water jet or by means of alternative cutting methods such as e.g. laser cutting. Once the piece has been weighed, the cutting line required to reduce this "overweight" piece to the desired weight can be calculated by a computer by optical volume detection and weight determination based on the density of the meat. In this case, the cutting line can advantageously be calculated in such a way as to minimise the quantity of off-cuts that cannot be used in the process. It is advantageous that practically no account has to be taken of the desired final shape of the product when calculating the cutting line.

Once the pieces have all been standardised to the desired weight, they are seasoned if desired and if this has not already taken place beforehand, and are prepared for the subsequent cooking process. To this end, preferably a marinade is used and the meat is processed in a tumbler. This method is generally known and leads to the marinade being rubbed in and to proteins being drawn out of the meat. As an alternative, a seasoning fluid may also be injected, which is introduced into the meat via a plurality of injection needles and is thus provided in a quicker and more effective manner, whereas the residence time in a tumbler is usually at least 15 minutes to an hour or more.

One particular advantage of the method according to the present invention is that the marinating can now be carried out using meat pieces having a meat mass which corresponds to the desired mass, and any off-cuts which are not required can be recycled without the marinade or supplied to another method. This is advantageous since purchasers usually wish to marinate the meat using their own marinade, so that off-cuts of marinated or tumbled meat could be reused only for these purchasers or even, if this purchaser does not permit clusters of individual pieces or pieces having the size of off-cuts, cannot be used further at all.

The meat pieces prepared as described above are now preshaped to the correct contour during the freezing process. This takes place in a particularly efficient manner by placing the meat on a transport device 13 that includes a transport belt 14 which contains freezing moulds or freezing cavities into which one portion is placed in each case. The freezing cavities may form part of the transport device by being shaping nests 16 formed in the transport belt 14. The portion may in this case be placed into the depression either by an automatic preshaping device 18 pressing device or manually. The preshaping device 18 may include either a placement device to place the meat into the freezing cavities or a pressing device to press the meat into the freezing cavities. Suction via a vacuum is also possible.

If the selected meat piece is very thin and wide, a funnel-type inlet may also be provided, via which the meat passes into the freezing mould either automatically or by the action of pressure. A special mechanism for folding a thin section could also be provided. This may for example automatically detect overhanging regions and fold them over so that they fall within the freezing mould.

The freezing cavities may advantageously be created in such a way as to prevent the meat pieces from freezing onto the freezing cavity during the freezing process or in such a way as to facilitate or allow the removal of frozen meat pieces from the moulds. To this end, the freezing cavity may be designed in two parts and/or in a flexible manner or may be provided with for example a hydrophobic coating. The coating may consist for example of an oil and/or may also be a solid coating which may include for example of a plastic, for example polytetrafluoroethylene. As an alternative or in addition to the described measures, the freezing cavities may subsequently also be heated via an external heat supply, either a heating system or a warm water bath, so that the edge regions thaw slightly for easier removal of the frozen meat.

After removal from the moulds, the meat pieces are supplied to the freezing station or facility 20, which deep-freezes the meat in the conventional manner. This may take place for example by a spiral froster or a tunnel froster. The temperature here is for example between −6 and −16° C.

In one preferred embodiment of the method, after deep-freezing, the individual pieces are removed from the freezing cavity and are supplied to a so-called "shaper" or shaping device 22 which then presses the meat pieces into the desired final shape. Here, the weight-controlled meat pieces may be reshaped by the known method DE 101 64 637 A1 in such a way that a product having a predefined three-dimensional shape is produced from each meat portion ("standardisation"). Alternatively, each meat portion may be transformed into a number of products having a predefined three-dimensional shape by the method DE 10 2005 016 159 A1 ("standard cutting").

For the present inventive optimisation of the method by the invention, it is important that the previously frozen meat piece during the intermediate step of preshaping has a shape which corresponds to or is smaller than the base surface area of the shaping cavity of the shaper. It is thus possible to prevent the punch of the shaper from cutting off a part of the meat which would then no longer fit into the shaping cavity. In addition, the degrees of deformation of the meat are reduced in the frozen state, which helps to achieve a gentler processing of the meat portion.

Finally, the preshaping carried out beforehand can also take account of the subsequent end product, since the preshaping takes place in such a way that it is not necessary to carry out extreme shaping solely by displacing the material in the shaper alone. Besides a shaping process that is gentle on the meat, this also means that a higher degree of flexibility is possible in terms of the design of the shaping cavity and that the cycle times can be reduced due to the lower degree of deformation that is required. The shaped meat products can then be supplied to any type of food processing; in particular, they can be coated with breadcrumbs and subjected to a cooking process by means of shallow frying, deep frying, steaming or boiling.

As a result of the method according to the present invention, a uniform size and equal weight can now be achieved for a large number of products made from a wide range of starting materials, regardless of the thickness of the meat product. It is thus possible to control both the portion size and shape.

The present invention also relates to a device for carrying out this method and to the product directly produced by the method and to all further products which contain such a product of the method.

The preferred example of embodiment of the method for producing shaped meat portions having a precise weight and with a predefined three-dimensional shape is carried out in such a way that natural meat pieces, which do not necessarily have the target weight and/or the target shape, enter the processing line and are firstly weighed. If the weight of the natural piece fortuitously happens to be the same as the target weight, this piece is conveyed further.

However, it is much more likely that the piece is either too small or too large. In the first-mentioned case, it is rejected and supplied to a different use. In the last-mentioned case, the desired weight can be achieved by cutting off a part of said piece. To this end, the volume of the piece is optically detected, the required cutting line is calculated based on the density, and then the piece is cut into one or more off-cuts and one piece which is suitable for the method.

The pieces thus selected, which correspond to the desired weight, are then seasoned and tumbled. The shaping step then takes place. In a first step, the meat is introduced into a freezing mould and is frozen. This results in a first preshaping.

In a second step, the frozen meat is then removed again from this mould and is finally brought to the desired three-dimensional shape in a shaper. To this end, the meat is placed into a shaping cavity of the shaper, the base surface area of which is somewhat larger than that of the freezing mould. This ensures that the meat securely remains in the mould during the subsequent pressing operation and is distributed in the desired manner, without being squeezed out of the mould at the sides.

The frozen portions thus produced can then be further divided in a conventional manner or further processed in some other way, for example coated in breadcrumbs or cooked.

The invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing description.

We claim:

1. A method for producing shaped meat portions, the method comprising the steps of sequentially:

introducing pieces of whole natural meat into a processing line;

determining respective weights of said introduced pieces;

combining a first set of those introduced pieces which do not reach said desired weight into a cluster of meat pieces that has said desired weight;

selecting a second set of those introduced pieces each having a weight which corresponds to said desired weight;

cutting down at least one piece of a third set of those introduced pieces having a weight which exceeds said desired weight such that the pieces of said third set each have said desired weight;

freezing said cluster of the first set of meat pieces, one piece of said second set of meat pieces having said desired weight, or one piece of said third set of meat pieces having cut down to said desired weight to form a frozen meat portion having said desired weight;

preshaping said frozen meat portion in a freezing mold such that it can be set in a cavity of a shaping device without extending past edges of the cavity;

deep freezing said preshaped frozen meat portion;

inserting said preshaped deep-frozen meat portin into the cavity of the shaping device; and shaping by the shaping device in the shaping cavity by either pressing or punching said preshaped deep frozen meat portion in a controlled manner and under action of pressure so as to form a shaped deep-frozen meat portion having a three-dimensional shape like that of the shaping cavity; and removing from said shaping cavity said shaped deep-frozen meat portion having a predefined weight and the predefined three-dimensional shape.

2. The method according to claim 1, wherein said third set of those introduced pieces are sorted so as to cut therefrom as many whole multiples of said desired weight as possible, wherein said whole multiples of said desired weight have said freezing, preshaping, deep freezing, shaping and removing processes performed thereon.

3. The method according to claim 1, wherein those ones of said third set of those introduced pieces having a weight such that at least when a foreseeable off cut of such a piece will again exceed said desired weight and thus a further meat piece can be produced therefrom, are divided in such a way that said meat portion and said off-cut come substantially to a shape of said shaping cavity.

4. The method according to claim 1, wherein in the case of said third set of those introduced pieces and prior to said cutting, said preshaping comprises rolling said third set of those introduced pieces into a shallow mold.

5. The method according to claim 1, wherein said preshaping comprises overlapping portions of one of said cluster of meat pieces, said second set of those introduced pieces having said desired weight or said third set of those introduced pieces having said desired weight within a mold prior to said freezing.

6. The method according to claim 1, wherein said frozen meat portion is removed from said mold and then separated and supplied to a shaping device comprising a plurality of shaping cavities.

7. The method according to claim 1, wherein said frozen meat portion is heated by a heating system or a warm water bath so as to improve removal of said frozen meat portion from said mold.

8. The method according to claim 1, wherein said mold is one of a plurality of molds in a transport belt which supplies said meat to a freezing station.

9. The method according to claim 1, wherein said shaping cavity is one of a plurality of shaping cavities, and said shaping comprises pressing and punching said frozen meat portion so as to form said shaped frozen meat portion.

10. The method according to claim 1, wherein said removed shaped frozen meat portion is reshaped to a different thickness, wherein to this end said removed shaped frozen meat portion is cut in a targeted manner such that a different degree of deformation occurs in said shaping cavity.

11. The method according to claim 1, wherein said shaped frozen meat portion is coated with breadcrumbs.

\* \* \* \* \*